United States Patent [19]
Barenberg et al.

[11] Patent Number: 5,965,264
[45] Date of Patent: Oct. 12, 1999

[54] POWDERS PROVIDING CONTROLLED SUSTAINED RELEASE OF A GAS

[75] Inventors: Sumner A. Barenberg; Peter N. Gray; Michael Lelah, all of Chicago, Ill.

[73] Assignee: Bernard Technologies, Inc., Chicago, Ill.

[21] Appl. No.: 08/921,357

[22] Filed: Aug. 29, 1997

Related U.S. Application Data

[60] Provisional application No. 60/026,273, Sep. 18, 1996.

[51] Int. Cl.$^6$ .................................................... A61L 2/16
[52] U.S. Cl. ............................ 428/402; 428/352; 428/353; 428/354; 428/402.24; 428/403; 428/407; 106/14.05; 106/14.21; 106/15.05; 422/5; 422/9; 424/76.1; 424/76.2; 424/76.21
[58] Field of Search .............................. 428/402, 402.24, 428/403, 407, 353, 354, 352; 106/15.05, 14.05, 14.21; 424/76.1, 76.2, 76.21; 422/5, 9

[56] References Cited

U.S. PATENT DOCUMENTS

| | | |
|---|---|---|
| 2,071,625 | 2/1937 | Haas et al. . |
| 2,482,891 | 9/1949 | Aston . |
| 2,546,568 | 3/1951 | Taylor . |
| 2,558,942 | 7/1951 | Eagleson . |
| 3,183,057 | 5/1965 | Marks et al. . |
| 3,585,147 | 6/1971 | Gordon . |
| 3,591,515 | 7/1971 | Lovely . |
| 3,767,787 | 10/1973 | Segal .......................................... 424/76 |
| 4,048,351 | 9/1977 | Saeman et al. .......................... 427/213 |
| 4,104,190 | 8/1978 | Hartshorn . |
| 4,330,531 | 5/1982 | Alliger .................................... 424/149 |
| 4,499,077 | 2/1985 | Stockel et al. ............................ 424/149 |
| 4,504,442 | 3/1985 | Rosenblatt et al. ........................ 422/37 |
| 4,547,381 | 10/1985 | Mason et al. ............................. 426/316 |
| 4,585,482 | 4/1986 | Tice et al. . |
| 4,681,739 | 7/1987 | Rosenblatt et al. ........................ 422/37 |
| 4,689,169 | 8/1987 | Mason et al. ......................... 252/186.24 |
| 4,728,498 | 3/1988 | Theeuwes .................................. 422/29 |
| 4,748,904 | 6/1988 | Razeto et al. .............................. 99/467 |
| 4,756,844 | 7/1988 | Walles et al. .............................. 252/95 |
| 4,829,129 | 5/1989 | Kelley .................................... 525/326.9 |
| 4,880,638 | 11/1989 | Gordon .................................... 424/662 |
| 4,889,654 | 12/1989 | Mason et al. .............................. 252/100 |
| 4,891,216 | 1/1990 | Kross et al. ................................ 424/78 |
| 4,925,645 | 5/1990 | Mason .................................... 423/477 |
| 4,956,184 | 9/1990 | Kross ...................................... 424/661 |
| 4,966,775 | 10/1990 | Donorio et al. .......................... 424/661 |
| 4,975,109 | 12/1990 | Friedman et al. ........................... 71/67 |
| 4,986,990 | 1/1991 | Davidson et al. ......................... 424/665 |
| 5,075,117 | 12/1991 | Kumami et al. .......................... 424/661 |
| 5,078,908 | 1/1992 | Ripley et al. ......................... 252/187.21 |
| 5,116,575 | 5/1992 | Badertscher et al. ....................... 422/28 |
| 5,126,070 | 6/1992 | Leifheit et al. ...................... 252/186.36 |
| 5,252,343 | 10/1993 | Kross ...................................... 424/661 |
| 5,278,112 | 1/1994 | Klatte ....................................... 502/62 |
| 5,306,440 | 4/1994 | Ripley et al. ........................ 252/186.33 |
| 5,360,609 | 11/1994 | Wellinghoff ........................... 514/772.3 |
| 5,384,134 | 1/1995 | Kross et al. .............................. 424/661 |
| 5,387,350 | 2/1995 | Mason ..................................... 210/754 |
| 5,399,288 | 3/1995 | Marzouk et al. .................... 252/186.21 |
| 5,405,549 | 4/1995 | Pitochelli ............................ 252/187.21 |
| 5,464,598 | 11/1995 | Klatte ...................................... 423/220 |
| 5,482,702 | 1/1996 | Murphy et al. ............................. 424/65 |
| 5,567,405 | 10/1996 | Klatte et al. ............................. 423/477 |
| 5,573,743 | 11/1996 | Klatte et al. ............................. 423/477 |
| 5,631,300 | 5/1997 | Wellinghoff ........................... 514/772.3 |
| 5,639,295 | 6/1997 | Wellinghoff et al. ................. 106/15.05 |
| 5,650,446 | 7/1997 | Wellinghoff et al. ................ 514/772.3 |
| 5,668,185 | 9/1997 | Wellinghoff ........................... 514/772.3 |
| 5,707,739 | 1/1998 | Wellinghoff et al. ................... 428/403 |

FOREIGN PATENT DOCUMENTS

| | | |
|---|---|---|
| 0 287 074 | 4/1988 | European Pat. Off. . |
| 0 611 162 | 2/1994 | European Pat. Off. . |
| 0 611 163 | 2/1994 | European Pat. Off. . |
| 57-198775 | 12/1982 | Japan . |
| 60058904 | 9/1983 | Japan . |
| 60-075231 | 4/1985 | Japan . |
| 60-092759 | 5/1985 | Japan . |
| 60-114171 | 6/1985 | Japan . |
| 60-130336 | 7/1985 | Japan . |
| 63-147469 | 6/1988 | Japan . |
| 63-246304 | 10/1988 | Japan . |
| 2055201 | 2/1990 | Japan . |
| 3184552 | 8/1991 | Japan . |
| 92004283 | 1/1992 | Japan . |
| 4-164005 | 6/1992 | Japan . |
| 4349104 | 12/1992 | Japan . |
| 6-107971 | 4/1994 | Japan . |
| 2151138 | 12/1984 | United Kingdom . |
| WO 85/04107 | 3/1985 | WIPO . |
| WO 88/09176 | 5/1988 | WIPO . |
| WO 96/18300 | 6/1996 | WIPO . |
| WO 96/39028 | 12/1996 | WIPO . |
| WO 96/39200 | 12/1996 | WIPO . |
| WO 96/39296 | 12/1996 | WIPO . |
| WO 96/41526 | 12/1996 | WIPO . |

*Primary Examiner*—Nathan M. Nutter
*Attorney, Agent, or Firm*—Senniger, Powers, Leavitt & Roedel

[57] ABSTRACT

A powder for sustained release of a gas including a core containing a molecular sieve, and a layer containing an acid releasing agent on an outer surface of the core. The core and the layer are substantially free of water, and the core is capable of generating and releasing a gas after hydrolysis of the acid releasing agent.

36 Claims, 2 Drawing Sheets

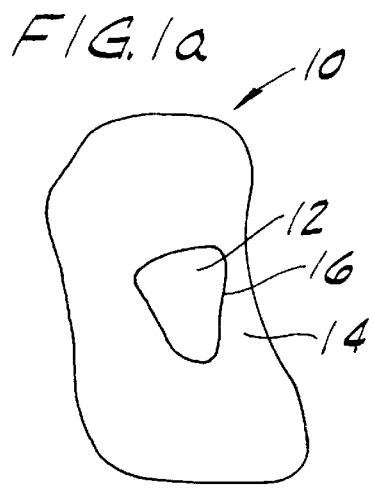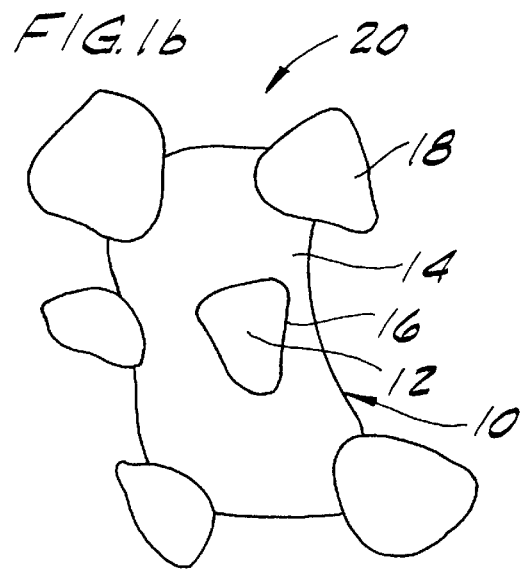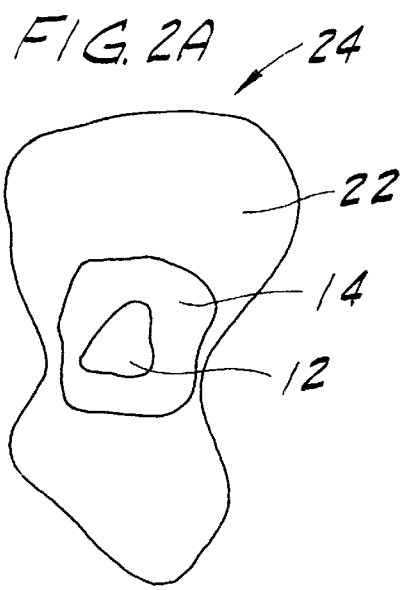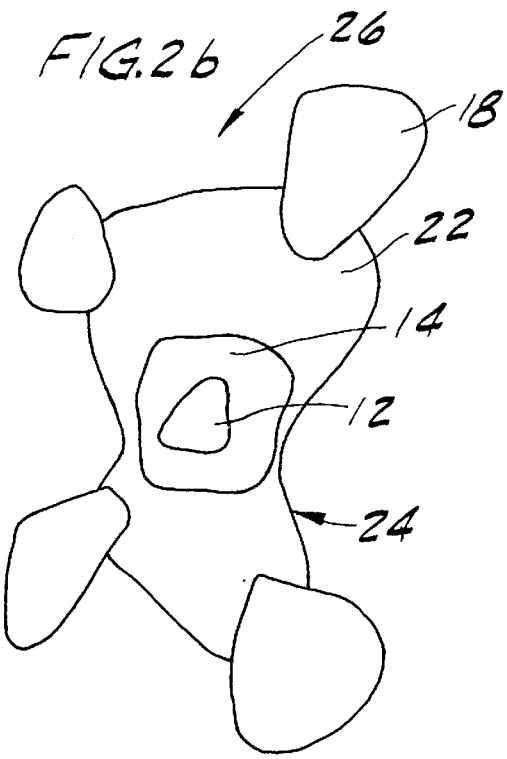

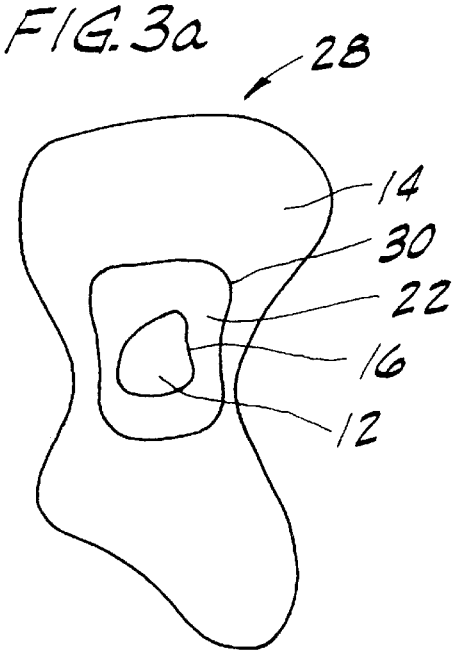
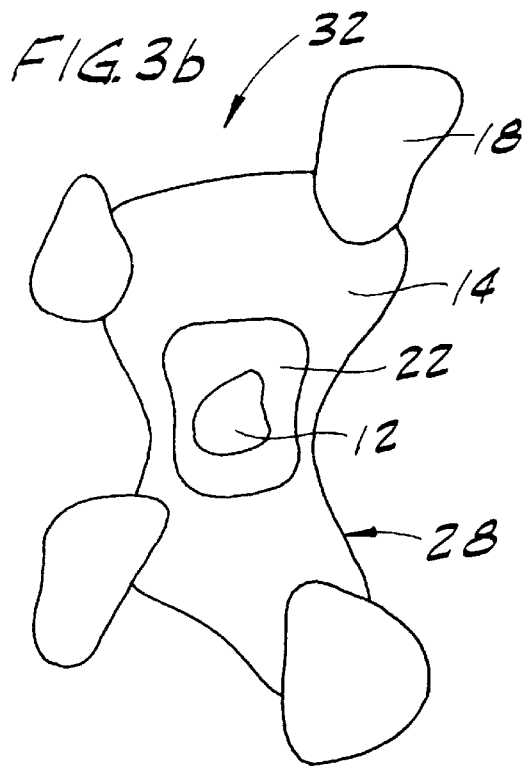
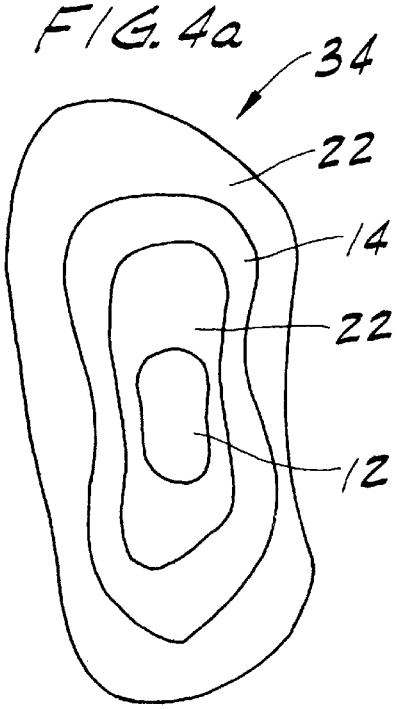
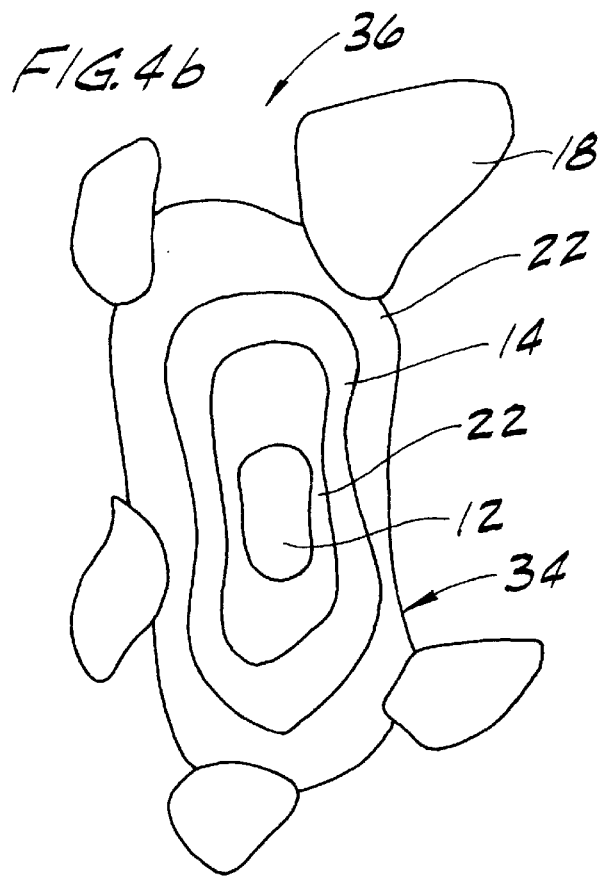

POWDERS PROVIDING CONTROLLED SUSTAINED RELEASE OF A GAS

REFERENCE TO RELATED APPLICATIONS

This application is a continuation-in-part application of provisional U.S. Ser. No. 60/026,273 filed Sep. 18, 1996.

BACKGROUND OF THE INVENTION

The present invention relates generally to a powder that provides sustained release of a gas. The invention particularly relates to a powder for retarding, controlling, killing or preventing microbiological contamination (e.g., bacteria, fungi, viruses, mold spores, algae, and protozoa), retarding, preventing or controlling biochemical decomposition, controlling respiration, deodorizing and/or retarding, preventing or controlling chemotaxis by release of a gas, such as chlorine dioxide, sulfur dioxide, nitrogen dioxide, nitric oxide, nitrous oxide, carbon dioxide, hydrogen sulfide, hydrocyanic acid, dichlorine monoxide, or chlorine.

Chlorine dioxide ($ClO_2$) is a superior oxidizing agent widely used as a bleach, disinfectant, fumigant or deodorizer. It can penetrate the cell wall or membrane and cytoplasm of mold spores, bacteria and other microbiological contaminants at concentrations below one part per million and destroy them.

The incorporation of chlorine dioxide or sodium chlorite in food packaging has prompted studies to determine whether residual levels of such preservatives result in a significant genetic or carcinogenic hazard to humans. Meier et al. studied the effect of subchronic and acute oral administration of chlorine, chlorine dioxide, sodium chlorite and sodium chlorate on the induction of chromosomal aberrations and spermhead abnormalities in mice [Environ. Mutagenesis, 7, 201 (1985)]. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Vilagines et al. attribute the relatively innocuous effect of chlorine dioxide to its inability to produce halomethanes, unlike hypochlorite and chlorine [Proc. AWWA Disinfect. Semin., 24 pp. (1977); Chem. Abs. 93, 173513f]. Recently, Richardson et al. reported that an extensive study of the reaction of chlorine dioxide with water borne organics by the Environmental Protection Agency confirmed this observation [Environ. Sci. Technol., 28, 592 (1994)].

Japanese Kokai Nos. 63/296,758, 63/274,434, and 57/168,977 describe deodorants containing chlorine dioxide incorporated in a polymer, ceramic beads, or calcium silicate wrapped in nonwoven cloth, respectively. Gels that generate chlorine dioxide for use as topical applications for disinfection are disclosed by Kenyon et al., Am. J. Vet. Res., 45(5), 1101 (1986). Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice et al., U.S. Pat. No. 4,585,482 describes gradual hydrolysis of alternating poly(vinyl methyl ether-maleic anhydride) or poly(lactic-glycolic acid) to generate acid that can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule. Solvents are required for reaction and application of the capsules. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems.

Powders that release chlorine dioxide as soon as they are prepared have been formed by mixing acid solids and chlorite solids. Lovely, U.S. Pat. No. 3,591,515 describes a chlorite-containing powder that releases chlorine dioxide upon being admixed with an acid-containing powder. Hartshorn, U.S. Pat. No. 4,104,190 describes solid mixtures of sodium chlorite and citric, adipic or malic acid that are compressed to form tablets. Mason et al., U.S. Pat. Nos. 4,547,381 and 4,689,169 disclose mixtures of powdered sodium chlorite, acid and inert diluent that release chlorine dioxide without exposing the mixtures to ambient moisture. Tice et al., U.S. Pat. No. 4,585,482 describes solid admixtures of sodium chlorite and polylactic acid.

Wellinghoff et al. have formulated composites that include a hydrophobic phase containing an acid releasing agent and a hydrophilic phase containing chlorite or other anions. The composite is substantially free of water and gas (e.g., chlorine dioxide) until it is exposed to moisture. Once exposed to moisture, acid and hydronium ions are generated in the hydrophobic phase. The hydronium ions migrate to the hydrophilic phase and react with the anions to generate a gas such as chlorine dioxide from the composite. These composites are composed of and generate only substances used in foods or substances generally recognized as safe or inert substances. The composites can be used for food packaging and other applications where the substances can be ingested by or in contact with humans or animals. These composites are described in U.S. Pat. Nos. 5,360,609, 5,631, 300, 5,639,295 and 5,650,446 and copending U.S. patent application Ser. Nos. 08/858,860, 08/858,859, 08/465,086, 08/461,716, and 08/461,304.

Wellinghoff et al. U.S. patent application Ser. No. 08/462, 039 discloses a composite formulated for maximum chlorine dioxide release in which the hydrophilic material contains an α-amino ether, ester or alcohol and a chlorite salt formed by reaction of an iminium chlorite and a base. Iminium chlorite is unstable to nucleophilic attack by the chlorite anion. When the iminium chlorite is reacted with a base, however, the more stable α-amino ether, ester or alcohol and a chlorite salt are formed.

Wellinghoff et al. U.S. patent application Ser. No. 08/726, 413 describes a method for maximizing chlorine dioxide release from an amine-containing composite by omitting the chlorite source until the composite is applied to a surface. After application, the composite is exposed to chlorine dioxide gas that either reacts with the amine to form iminium chlorite in situ or reacts with the amine to provide chlorite anions. The composite is then activated in the presence of moisture to release chlorine dioxide. The composite can be exposed to elevated temperatures during processing, storage and application because the hydrophilic material does not contain iminium chlorite or any chlorite anions that could decompose at such temperatures. The method also precludes premature release of chlorine dioxide from the composite.

Barenberg et al. U.S. patent application Ser. No. 08/724,907 and Wellinghoff et al. U.S. patent application Ser. No. 08/858,860 describe numerous methods of using composites such as those disclosed by Wellinghoff et al. to retard bacterial, fungal, and viral contamination and growth of molds on food, produce, meat, and other materials and to deodorize materials such as textiles and storage spaces.

Wellinghoff et al. U.S. patent application Ser. No. 08/651,876 describes transparent compositions that provide sustained release of chlorine dioxide.

There is a need for an inert powder that can be easily activated to initiate release of chlorine dioxide or another biocidal or deodorizing gas in use. A powder that is composed of and generates only substances used in foods, or those generally recognized as safe or inert substances, is particularly needed for food packaging, modified atmosphere packaging, and other applications where the substances can be ingested by or in contact with humans. Although the Wellinghoff et al. composites are effective biocides, there is a need for biocidal compositions that can be more readily manufactured and provide more control or flexibility for sustained release of a gas.

SUMMARY OF THE INVENTION

Among the objects of the invention, therefore, may be noted the provision of a powder that releases a concentration of chlorine dioxide or other biocidal gas sufficient to eliminate bacteria, fungi, molds, algae, protozoa and viruses; the provision of a powder that releases a concentration of a gas that retards, prevents or controls biochemical decomposition, controls respiration, retards, prevents or controls chemotaxis, or deodorizes; the provision of such a powder that releases such gas concentrations after activation for a period of up to several months; the provision of such a powder that begins to release a gas within minutes, hours, days, weeks or months after being activated by moisture; the provision of such a powder that is free-flowing and can be easily blended with other ingredients prior to application; the provision of such a powder that can penetrate porous surfaces; the provision of such a powder that increases the release rate of chlorine dioxide or other gas in proportion to increased levels of temperature and humidity, which promote mold and bacteria growth; and the provision of such a powder that only releases substances approved for human exposure or ingestion.

The present invention is directed to a powder for sustained release of a gas including a core containing a molecular sieve, and a layer containing an acid releasing agent on an outer surface of the core. The core and the layer are substantially free of water, and the core is capable of generating and releasing a gas after hydrolysis of the acid releasing agent.

Another embodiment of the invention is directed to a powder for sustained release of a gas including a core containing a molecular sieve, a first layer containing an acid releasing agent, and a second layer between the core and the first layer. The second layer contains a hydrophobic material, a water-soluble material, a water-degradable material, or a water-swellable material. The core and the first and second layers are substantially free of water, and the core is capable of generating and releasing a gas after hydrolysis of the acid releasing agent.

Yet another embodiment of the invention is directed to a process for preparing a powder providing sustained release of a gas by admixing molecular sieve particles containing anions with an acid releasing agent to form a product, and fragmenting the product to form a powder. The powder is substantially free of water and capable of generating and releasing the gas after hydrolysis of the acid releasing agent.

Another embodiment of the invention is directed to a method of retarding, killing, preventing or controlling microbiological contamination on a surface of a material, within the material or in the atmosphere surrounding the material, by exposing a surface of a material to the powder, and exposing the surface to moisture to generate and release a biocidal gas from the powder into the atmosphere surrounding the surface.

The invention is also directed to a method of retarding, killing, preventing or controlling microbiological contamination on a surface of a material, within the material or in the atmosphere surrounding the material, by placing a material adjacent the powder, and exposing the powder to moisture to release a biocidal gas from the powder into the atmosphere surrounding the material.

The invention is also directed to a method of retarding, preventing or controlling biochemical decomposition on a surface of a material or within the material by exposing a surface of a material to a powder of the invention, and exposing the surface to moisture to generate and release a biochemical decomposition-inhibiting gas from the powder into the atmosphere surrounding the surface.

Another embodiment of the invention is directed to a method of retarding, preventing or controlling biochemical decomposition on a surface of a material or within the material by placing the material adjacent a powder of the invention, and exposing the powder to moisture to release a biochemical decomposition-inhibiting gas from the powder into the atmosphere surrounding the material.

Yet another embodiment of the invention is a method of controlling respiration of a material by exposing a surface of a material to a powder of the invention, and exposing the surface to moisture to generate and release a respiration-controlling gas from the powder into thee atmosphere surrounding the surface.

Another embodiment of the invention is a method of controlling respiration of a material by placing the material adjacent a powder of the invention, and exposing the powder to moisture to release a respiration-controlling gas from the powder into the atmosphere surrounding the material.

The invention is also directed to a method of deodorizing a surface of a material or the atmosphere surrounding the material, by exposing a surface of a material to the powder, and exposing the surface to moisture to generate and release a deodorizing gas from the powder into the atmosphere surrounding the surface.

Yet another embodiment of the invention is directed to a method of deodorizing a surface of a material or the atmosphere surrounding the material, by placing a material adjacent the powder, and exposing the powder to moisture to release a deodorizing gas from the powder into the atmosphere surrounding the material.

Another embodiment of the invention is directed to a method of retarding, preventing or controlling chemotactic attraction of an organism to a material, by exposing a surface of a material to the powder, and exposing the surface to moisture to generate and release an odor-masking or odor-neutralizing gas from the powder into the atmosphere surrounding the surface.

The invention is also directed to a method of retarding, preventing or controlling chemotactic attraction of an organism to a material, by placing a material adjacent the powder, and exposing the powder to moisture to release an odor-masking or odor-neutralizing gas from the powder into the atmosphere surrounding the material.

Other objects and advantages of the invention will be apparent from the following detailed description.

BRIEF DESCRIPTION OF THE DRAWINGS

FIGS. 1a–4b are schematics of particles for providing sustained release of a gas.

DETAILED DESCRIPTION OF THE PREFERRED EMBODIMENTS

In accordance with the present invention, it has been discovered that sustained release of a gas can be generated from a powder containing a molecular sieve core encased within an acid releasing agent when the powder is exposed to moisture. The molecular sieve core contains anions such as chlorite which are used to generate a gas when the powder is used. Although anions such as chlorite, bisulfite and bicarbonate can decompose at typical processing temperatures, the particles of the invention are thermally stable because the anions are impregnated within pores of a molecular sieve that is encapsulated by at least one coating layer to protect the anions from thermal decomposition. The powder formed from such particles can be processed at relatively high temperatures as compared to sodium chlorite, bisulfite or bicarbonate and provides sustained release of a gas. Release of gas from the particle is controlled by surrounding the core with an acid releasing agent, and optionally, a hydrophobic material, a dispersant, anhydrous particles, a water-soluble material, a water-degradable material or a water-swellable material to delay release of gas from the powder for minutes to months after activation by moisture. The powder is easily prepared and can be used as is or incorporated into various end-use products, such as films, formed objects, adhesives, granular blends, and powdered compositions.

In one embodiment of the invention as shown in FIG. 1a, a powder is comprised of a plurality of particles 10 including a core 12 having an acid releasing layer 14 on an outer surface 16 of the core. The core 12 includes a molecular sieve containing anions that are capable of reacting to generate a gas. Although the acid releasing layer 14 is preferably continuous and substantially uniform, a particle 10 having a discontinuous acid releasing layer of variable thickness provides acceptable, sustained release of a gas.

FIG. 1b illustrates another embodiment of the invention wherein particles 18 contact the acid releasing layer 14 of the particle 10 as shown in FIG. 1a to form a particle 20. The particles 18 contain an anhydrous material capable of binding with water. For purposes of the present invention, an anhydrous material does not contain water, such as adsorbed water or water of crystallization.

When a powder of the invention is exposed to ambient moisture or otherwise contacted with water, the water diffuses into the acid releasing layer 14. If the powder includes particles 18, the water binds to the particles 18 on the outer surface of the powder before diffusing into the layer 14. The acid releasing agent within the layer 14 is either an acid or a substance that can be hydrolyzed to an acid (i.e., a substance that reacts with the water that diffuses into the layer 14 to form an acid). In either case, the acid in the layer 14 dissolves in the water that diffuses into the layer, forming hydronium ions and a counterion. The reaction products of this hydrolysis reaction are hydronium ions and counterions when the reaction proceeds to completion, or hydrconium ions, counterions, acid and water when the reaction is in equilibrium. The hydronium ions resulting from the acid hydrolysis diffuse from the layer 14 into pores (not shown) of the core 12, where they react with anions to generate a gas. The gas diffuses out of the powder into the surrounding atmosphere for a period of up to about six months to affect materials situated near the powder. Powders that release at least about $1.0\times10^{-6}$ gram gas/$cm^3$ for a period of at least one day, one week, one month or six months can be formulated by the processes of the present invention for a variety of end uses, including deodorization, chemotaxis control, delay or prevention such as reduction of insect infestation, biochemical decomposition control, reduction or prevention, respiration control, and control, delay, destruction or prevention of the growth of microorganisms such as bacteria, molds, fungi, algae, protozoa, and viruses on materials. Although the powders generally provide sustained release of a gas, the powders can be formulated so that gas release during less than one day if desired for a particular end use.

In another embodiment illustrated in FIG. 2a, the particle 10 as shown in FIG. 1a is surrounded by a layer 22 containing a hydrophobic, water-soluble, water-degradable or water-swellable material to form a particle 24. In FIG. 2b, the particle 24 of FIG. 2a is contacted with the particles 18 to form a particle 26. When the particle 10 coated with a water-soluble or water-degradable material is exposed to moisture, the water dissolves or degrades the material for a period of up to six months, preferably from several hours to one month, before water contacts the acid releasing agent. When the particle 10 coated with a water-swellable material is exposed to moisture, the water diffuses into the material and causes the material to expand for a period of up to six months, preferably from several hours to one month, before water contacts the acid releasing agent. Coating the particle 10 with a hydrophobic material also prolongs the diffusion of water into the acid releasing layer for a period of up to six months, preferably from several hours to one month. Gas release does not occur until enough moisture is adsorbed by the hydrophobic layer 22 to provide a pathway for interdiffusion between the layers 14 and 22. After the water enters the acid releasing layer, gas release occurs according to the mechanism described above. Although the layers 14 and 22 are preferably continuous and substantially uniform, a particle 24 or 26 having discontinuous layers 14 and 22 of variable thickness provides acceptable, sustained release of a gas.

FIG. 3a illustrates a particle 28, another embodiment of the invention, in which the layer 22 containing the hydrophobic, water-soluble, water-degradable or water-swellable material contacts the outer surface 16 of the core 12. The acid releasing layer 14 contacts an outer surface 30 of the layer 22 such that the layer 22 separates the core 12 from the acid releasing layer 14 and delays diffusion of hydronium ions into the core. In FIG. 3b, the particle 28 of FIG. 3a is contacted with the particles 18 to form a particle 32. When the acid releasing layer 14 is exposed to moisture, the acid releasing agent is hydrolyzed, releasing acid and hydronium ions which diffuse from the acid releasing layer to the layer 22. The hydronium ions do not diffuse into the core 12 until enough hydronium ions are present in the layer 22 to provide a pathway for interdiffusion between the layer 22 and the core. The layer 22 controls the release of gas by prolonging diffusion of hydronium ions into the core to delay their reaction with anions within the core as described above. Although the layers 14 and 22 are preferably continuous and substantially uniform, a particle 28 or 32 having discontinuous layers 14 and 22 of variable thickness provides acceptable, sustained release of a gas.

In another embodiment illustrated in FIG. 4a, the particle 28 as shown in FIG. 3a is surrounded by an outer layer 22 containing a hydrophobic, water-soluble, water-degradable or water-swellable material to form a particle 34. The outer layer 22 controls gas release by delaying diffusion of water into layer 14 until enough moisture is adsorbed by the layer 22 to provide a pathway for interdiffusion between the layers 14 and 22. The inner layer 22 also controls gas release by delaying diffusion of hydronium ions into the core 12 until enough hydronium ions are present in the layer 22 to provide a pathway for interdiffusion between the layer 22 and the core. In FIG. 4b, the particle 34 of FIG. 4a is contacted with the particles 18 to form a particle 36. Although the layers 14 and 22 are preferably continuous and substantially uniform, a particle 34 or 36 having discontinuous layers 14 and 22 of variable thickness provides acceptable, sustained release of a gas.

The core 12, the acid releasing layer 14, the layer 22, and the particles 18 are substantially free of water to avoid release of gas prior to use of the powder. For purposes of the present invention, the core 12, the layers 14 and 22, and the particles 18 are substantially free of water if the amount of water in the powder does not provide a pathway for transmission of hydronium ions from the acid releasing layer to the core. Preferably, each of the core 12, the layers 14 and 22, and the total particles 18 embedded in the outer layer of the particles 20, 26, 32 or 36 can include up to about 0.1 wt. % water and, more preferably up to about 0.05 wt. % water, without providing such a pathway for interdiffusion between the core and the acid releasing layer. Insubstantial amounts of water can hydrolyze a portion of the acid releasing agent to produce acid and hydronium ions within the acid releasing layer. The hydronium ions, however, do not diffuse into the core until enough free water is present for transport of hydronium ions.

The powders of the invention can include coatings (i.e., additional layers) between the core 12 and the layers 14 and 22 so long as the coatings do not prevent the diffusion of hydronium ions from the acid releasing layer 14 to the core 12 or diffusion of gas from the powder.

The rate of gas release from a powder and the release rate profile can be altered in various ways, such as by changing the temperature of the powder, changing the concentration of acid releasing agent, hydrophobic material, or water-soluble, water-degradable, or water-swellable material in the powder, adding a desiccant or humectant to the powder to control release of gas once the powder is exposed to moisture, changing the hydrophobicity of the acid releasing agent by changing the nature of the acid generative moiety therein, changing the powder microstructure, substituting alternative hydrophobic materials or anhydrous particles, changing the method of processing the powder, or changing the order of addition of ingredients in preparing the powder.

Preferably, the powder comprises between about 5 wt. % and about 95 wt. % core, between about 5 wt. % and about 95 wt. % acid releasing layer, up to about 50 wt. % hydrophobic, water-soluble, water-degradable or water-swellable material, and up to about 95 wt. % of the particles 18. More preferably, the powder comprises between about 15 wt. % and about 95 wt. % core, between about 15 wt. % and about 95 wt. % acid releasing layer, between about 10 wt. % and about 40 wt. % hydrophobic, water-soluble, water-degradable or water-swellable material, and between about 10 wt. % and about 50 wt. % of the particles.

Preferably, the core of the powder comprises between about 60 wt. % and about 98 wt. % molecular sieve, between about 2 wt. % and about 10 wt. % anions capable of reacting to generate a gas, and up to about 90 wt. % base. More preferably, the core comprises between about 90 wt.% and about 98 wt. % molecular sieve, between about 2 wt. % and about 10 wt. % anions capable of reacting to generate a gas, and between about 5 wt. % and about 30 wt. % base.

The acid releasing layer of the powder preferably comprises between about 10 wt. % and 100 wt. % acid releasing agent, up to about 80 wt. % diluent and up to about 20 wt. % dispersant, and, more preferably, between about 40 wt. % and about 90 wt. % acid releasing agent, between about 10 wt. % and about 60 wt. % diluent and between about 5 wt. % and about 15 wt. % dispersant.

When the powder includes one hydrophobic, water-soluble, water-degradable or water-swellable layer 22, the layer 22 preferably contains between about 10 wt. % and 100 wt. % hydrophobic, water-soluble, water-degradable or water-swellable material, up to about 80 wt. % diluent and up to about 20 wt. % dispersant, and, more preferably, between about 40 wt. % and about 90 wt. % hydrophobic, water-soluble, water-degradable or water-swellable material, between about 10 wt. % and about 60 wt. % diluent and between about 5 wt. % and about 15 wt. % dispersant.

When the powder includes two layers 22, the layer 22 separating the core 12 from the acid releasing layer 14 preferably contains between about 10 wt. % and 100 wt. % hydrophobic, water-soluble, water-degradable or water-swellable material, up to about 80 wt. % diluent and up to about 20 wt. % dispersant, and, more preferably, between about 40 wt. % and about 90 wt. % hydrophobic, water-soluble, water-degradable or water-swellable material, between about 10 wt. % and about 60 wt. % diluent and between about 5 wt. % and about 15 wt. % dispersant. The outer layer 22 preferably contains between about 10 wt. % and 100 wt. % hydrophobic, water-soluble, water-degradable or water-swellable material, up to about 80 wt. % diluent and up to about 20 wt. % dispersant, and, more preferably, between about 40 wt. % and about 90 wt. % hydrophobic, water-soluble, water-degradable or water-swellable material, between about 10 wt. % and about 60 wt. % diluent and between about 5 wt. % and about 15 wt. % dispersant.

The core of each particle is generally a molecular sieve particle containing anions. Any molecular sieve can be used in the powders of the invention including natural and synthetic molecular sieves. Suitable molecular sieves include natural and synthetic zeolites such as clinoptiloite, analcite, analcime, chabazite, heulandite, natrolite, phillipsite, stilbite, thomosonite and mordenite, crystalline aluminophosphates, ferricyanides and heteropolyacids. Molecular sieves generally have a pore size ranging from about 5 to 10 Angstroms, and a particle size ranging from about 10 micrometers to about one centimeter.

The core of the powder also contains anions which react with hydronium ions to form a gas. The anions are generally provided by salts of the anions and a counterion. Preferred salts include sodium, potassium, calcium, lithium or ammonium salts of a chlorite, bisulfite, hydrosulfide, bicarbonate, hypochlorite, nitrite, or cyanide.

The core can also include a base to control release of gas from the powder. When a base is included in the core, hydronium ions formed in the acid releasing layer diffuse into the core and react with the base to form a salt. When the base is depleted, excess hydronium ions then react with the anions within the core to form a gas. The amount of base within the pores of the core can be adjusted to alter the time period before gas is released from the particle. For example, the concentration of the base can be increased if a longer delay of gas release is desired.

Any base that reacts with a hydronium ion can be incorporated in the core. Suitable bases include but are not limited to, an alkali metal bicarbonate such as lithium, sodium, or potassium bicarbonate, an alkali metal carbonate such as lithium, sodium or potassium carbonate, an alkaline-earth metal bicarbonate, an alkaline-earth metal carbonate such as magnesium or calcium carbonate, a bicarbonate salt of a transition metal ion or a protonated primary, secondary, tertiary or quaternary amine such as ammonium bicarbonate, a carbonate salt of a transition metal ion or a protonated primary, secondary, tertiary or quaternary amine, an alkali metal hydroxide such as lithium, sodium or potassium hydroxide, an alkaline-earth metal hydroxide such as calcium or magnesium hydroxide, a hydroxide salt of a transition metal ion or a protonated primary, secondary, tertiary or quaternary amine such as ammonium hydroxide, an alkali metal biphosphate such as sodium biphosphate, an alkali metal phosphate such as sodium, dipotassium or tripotassium orthophosphate or potassium diphosphate, an alkaline-earth metal biphosphate such as calcium biphosphate, an alkaline-earth metal phosphate such as bicalcium or tricalcium phosphate, a biphosphate salt of a transition metal ion or a protonated primary, secondary, tertiary or quaternary amine such as ammonium biphosphate, a phosphate salt of a transition metal ion or a protonated primary, secondary, tertiary or quaternary amine, an alkali metal bisulfate such as sodium or potassium bisulfate, an alkali metal sulfate such as sodium or potassium sulfate, an alkaline-earth metal bisulfate, an alkaline-earth metal sulfate such as calcium or magnesium sulfate, a bisulfate salt of a transition metal ion or a protonated primary, secondary, tertiary or quaternary amine such as ammonium bisulfate, a sulfate salt of a transition metal ion or a protonated primary, secondary, tertiary or quaternary amine such as ammonium sulfate, an alkali metal sulfonate such as sodium sulfonate, an alkaline-earth metal sulfonate, or a sulfonate salt of a transition metal ion or a protonated primary, secondary, tertiary or quaternary amine, an alkali metal borate such as borax, an alkaline-earth metal borate such as magnesium orthoborate, or a borate salt of a transition metal ion or a protonated primary, secondary, tertiary or quaternary amine.

The gas released by the powder will depend upon the anions within the core. Any gas that is formed by reaction of a hydronium ion and an anion can be generated and released by the powder. The gas is preferably chlorine dioxide, sulfur dioxide, hydrogen sulfide, hydrocyanic acid, nitrogen dioxide, nitric oxide, nitrous oxide, carbon dioxide, dichlorine monoxide, or chlorine.

Chlorine dioxide gas is released if the core contains a source of chlorite anions. Suitable chlorite sources that can be incorporated into the core include alkali metal chlorites such as sodium chlorite or potassium chlorite, alkaline-earth metal chlorites such as calcium chlorite, or chlorite salts of a transition metal ion or a protonated primary, secondary, tertiary or quaternary amine such as ammonium chlorite, trialkylammonium chlorite, and quaternary ammonium chlorite. Many chlorite sources, such as sodium chlorite, are stable at processing temperatures in excess of about 100° C., allowing for processing at relatively high temperatures. Chlorine dioxide-releasing powders can be used to deodorize, retard, prevent or control chemotaxis, retard, prevent or control biochemical decomposition, or to kill, retard, control or prevent the growth of bacteria, molds, fungi, algae, protozoa, and viruses.

Sulfur dioxide is released if the core contains bisulfite anions. Bisulfite sources that can be incorporated into the core include alkali metal bisulfites such as sodium bisulfite or potassium bisulfite, alkaline-earth metal bisulfites such as calcium bisulfite, or bisulfite salts of a transition metal ion or a protonated primary, secondary, tertiary or quaternary amine. Sulfur dioxide gas-releasing powders can be used for food preservation (e.g. to inhibit biochemical decomposition such as browning of produce), disinfection, and inhibition of enzyme-catalyzed reactions. The powders can also be used for reduction of chlorine gas concentration in catalytic cycles where aluminum or iron powder is used to selectively scrub chlorine from a mixture of chlorine and chlorine dioxide. The powders are also useful in modified atmosphere packaging by placing the powder within a package and sealing the package to create a sulfur dioxide atmosphere within the package.

Hydrogen sulfide is released from a core containing hydrosulfide anions. Acceptable sources of hydrosulfide anions include alkali metal hydrosulfides such as sodium hydrosulfide or potassium hydrosulfide, alkaline-earth metal hydrosulfides such as calcium hydrosulfide, or hydrosulfide salts of a transition metal ion or a protonated primary, secondary, tertiary or quaternary amine. Hydrogen sulfide gas-releasing powders can be used as a reducing agent or a sulfur source in the manufacture of chemicals, and as a polymerization inhibitor.

Chlorine gas and dichlorine monoxide are released from a core containing hypochlorite anions. Acceptable sources of hypochlorite anions include alkali metal hypochlorites such as sodium hypochlorite, alkaline-earth metal hypochlorites such as calcium hypochlorite, or hypochlorite salts of a transition metal ion or a protonated primary, secondary, tertiary or quaternary amine. Chlorine gas-releasing powders can be used in processing meat, fish and produce and as an insecticide. Dichlorine monoxide releasing powders can be used as a biocide.

Hydrocyanic acid is released from a core if it contains a source of cyanide anions. Suitable sources of cyanide anions include alkali metal cyanides such as sodium cyanide or potassium cyanide, alkaline-earth metal cyanides such as calcium cyanide, or cyanide salts of a transition metal ion or a protonated primary, secondary, tertiary or quaternary amine. Hydrocyanic acid gas-releasing powders can be used as a pesticide or a rodenticide.

Carbon dioxide gas is released if a core contains a source of bicarbonate anions. Suitable bicarbonate sources that can be incorporated into the core include alkali metal bicarbonates such as sodium bicarbonate, potassium bicarbonate, or lithium bicarbonate, alkaline-earth metal bicarbonates, or bicarbonate salts of a transition metal ion or a protonated primary, secondary, tertiary or quaternary amine such as ammonium bicarbonate. Carbon dioxide gas-releasing powders can be used in greenhouses by applying it to the soil surface to enrich the air surrounding plants. The carbon dioxide-releasing powders can also be used in modified atmosphere packaging by placing the powder within a package and sealing the package to create a carbon dioxide atmosphere within the package. The package can then be used to control respiration of produce, cut flowers or other plants during storage and transportation, or to retard, prevent or control biochemical decomposition of foods.

Nitrogen dioxide and nitric oxide are released from a core if it contains a source of nitrite anions. Suitable sources of nitrite anions include alkali metal nitrites such as sodium nitrite or potassium nitrite, alkaline-earth metal nitrites such as calcium nitrite, or nitrite salts of a transition metal ion or a protonated primary, secondary, tertiary or quaternary amine. Nitrogen dioxide or nitric oxide gas-releasing powders can be used to improve biocompatibility of biomaterials and for modified atmosphere packaging.

In some instances, powders having a core containing two or more different anions are effective in controlling release of a gas. The powder illustrated in FIG. 1a, for example, can be prepared by admixing core particles containing chlorite anions and core particles containing bisulfite anions into the liquid containing an acid releasing agent to form the coated particles. If chlorine dioxide and sulfur dioxide are released in preparing the powder, the sulfur dioxide reduces the chlorine dioxide to chlorite, controlling release of chlorine dioxide from the powder. The presence of bisulfite anions in the core also delays chlorine dioxide release from the powder during storage to avoid reaction of chlorine dioxide with powder additives such as fragrances. Powders containing two or more different anions in the core can also release two or more different gases for different purposes. For example, a powder containing bisulfite and chlorite anions can release sulfur dioxide for food preservation and chlorine dioxide for deodorization or control of chemotaxis.

Any acid releasing agent that is capable of being hydrolyzed by ambient moisture and adhered onto a particle or incorporated in a coating to be applied to a particle is acceptable for purposes of the present invention. Preferably, the acid releasing agent does not react with the core in the absence of moisture, and does not exude or extract into the environment. Suitable acid releasing agents include carboxylic acids, esters, anhydrides, acyl halides, phosphoric acid, phosphate esters, trialkylsilyl phosphate esters, dialkyl phosphates, sulfonic acid, sulfonic acid esters, sulfonic acid chlorides, phosphosilicates, phosphosilicic anhydrides, carboxylates of poly α-hydroxy alcohols such as sorbitan monostearate or sorbitol monostearate, and phosphosiloxanes. Examples of such acid releasing agents include an anhydride or phosphate ester blended with or grafted to polypropylene, polyethylene or polystyrene, or trimethylsilyl phosphate esters of the formulae

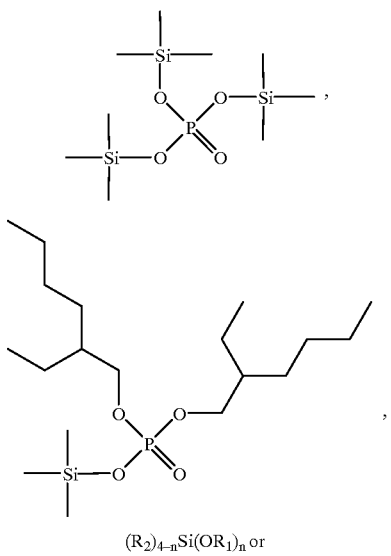

$CH_3SiOP(O)(OR)_2$ wherein R is a non-hydrogen bonding group, alkyl or aryl, $R_1$ and $R_2$ are alkyl, alkoxy or aryl and n is 1–25. Water-hydrolyzable acid releasing polymers or oligomers are preferred.

Linear or star like oligomers (e.g., a micelle like molecule with a lipid wall and a P—O—Si core), such as a phosphosilicic anhydride that is the reaction product of a phosphoric acid ester of a $C_4$ to $C_{27}$ organic compound and a silicate ester, are preferred acid releasing agents. Preferred phosphosilicic anhydrides of esters have the formula

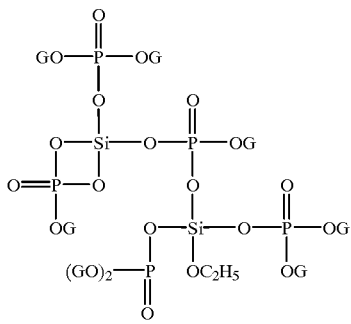

wherein G is a carboxylic acid ester of a polyhydric alcohol and a $C_4$ to $C_{27}$ hydrocarbon, which has the formula

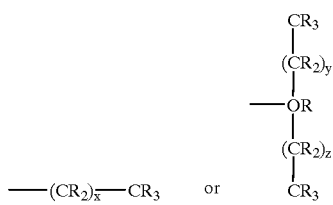

wherein each R is individually selected from hydrogen, hydroxy, alkyl, alkenyl, or —OC(O)R'; R' is a $C_4$ to $C_{27}$ alkyl or $C_4$ to $C_{27}$ alkenyl; x is an integer from 1 to 30; y is an integer from 0 to 30; and z is an integer from 0 to 30. Particularly preferred phosphosilicic anhydrides of polyol based esters include alkylene glycol fatty acid ester acid releasing waxes such as propylene glycol monostearate acid releasing wax having the formula

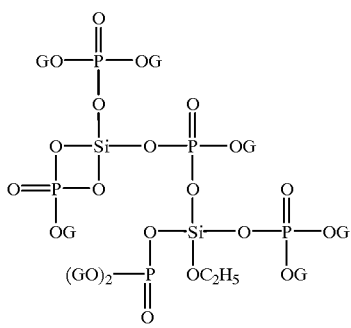

wherein G is

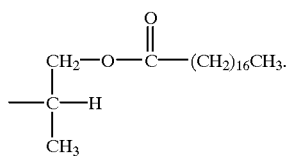

A preferred phosphosilicic anhydride of a glycerol based ester, known as LPOSI or glycerol monostearate acid releasing wax, has the formula

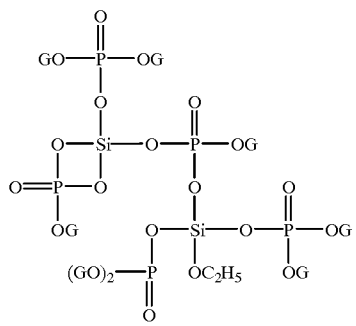

wherein G has the formula

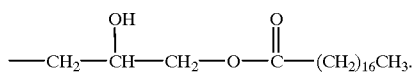

Other preferred acid releasing agents have the formulae:

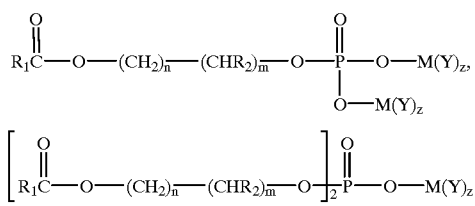

wherein $M(Y)_z$ is an oligomeric radical in which Y is a portion of a multifunctional oxide structure and M is a group IIIA, IVA, or IVB element such as titanium, aluminum, tin, or silicon;; $R_1$ is an alkyl group; $R_2$ is methyl, ethyl, propyl, a methyl amido, or an ethyl amido group; m is 0, 1, 2 or 3; n is 0, 1, 2 or 3; and z is 2 or 3.

Acid anhydrides are also preferred acid releasing agents and include organic acid anhydrides, mixed organic acid anhydrides, homopolymers of an organic acid anhydride or a mixed inorganic acid anhydride, and copolymers of an organic acid anhydride or a mixed inorganic acid anhydride with a monomer containing a double bond. Preferred mixed inorganic acid anhydrides contain a phosphorus-oxygen-silicon bond. Preferred anhydrides include copolymers of maleic anhydride, methacrylic anhydride, acetic anhydride, propionic anhydride, or succinic anhydride, and vinyl, styrene or an alkene, such as maleic anhydride-styrene copolymers, or grafts thereof with olefins such as polypropylenes, polyethylenes, or polystyrenes. Copolymers of acid anhydrides and esters of lactic or glycolic acids can provide a rapid initial gas release rate followed by a slow release rate.

A diluent can be included in the acid releasing layer 14. The diluent is any hydrophobic material that can be applied to the core and solidified to form a layer on the core. Preferred diluents include microcrystalline wax, paraffin wax, synthetic wax such as chlorinated wax or polyethylene wax, or a polymer such as atactic polypropylene, polyolefin, or polyester, or polymer blends, multicomponent polymers such as copolymers, terpolymers or oligomers, or polymer alloys thereof. These diluents are commercially available from various sources. Preferred microcrystalline waxes include the Astorwax microcrystalline waxes commercially available from Astor Wax Corp., Doraville, Ga. Diluents are preferably incorporated in the acid releasing layer if the acid releasing agent is not hydrophobic.

The dispersant in the acid releasing layer 14 is any substance that minimizes agglomeration of the core particles during preparation of the powder, controls release of the gas from the powder, lowers the surface reactivity of the core, and does not react with i:he core. Substances having hydrophilic and hydrophobic portions are preferred. The hydrophilic portion of the substance can be absorbed by the surface of the core. The hydrophobic portion of the substance minimizes agglomeration of the core particles when the particles are mixed. Preferred dispersants that can be incorporated into the layer 14 have a melting point not greater than 220° C., and include amides of carboxylates such as amide isostearates, polyvinyl acetates, polyvinyl alcohols, polyvinylpyrrolidone copolymers, polyethylene glycols, and metal carboxylates such as zinc isostearate. Dispersants having a melting point greater than 50° C. are preferably admixed with the core particles before being admixed with the acid releasing agent. Suitable polyvinylpyrrolidone copolymers include copolymers of polyvinylpyrrolidone and hexadecane such as Ganex V-216, and copolymers of polyvinylpyrrolidone and eicosene such as Ganex V-220, which are commercially available from GAF Corp.

The hydrophobic material of layer 22 is any hydrophobic material that can be applied to the core or layer 14 and solidified to form a layer on the core or layer 14. Suitable hydrophobic materials are the diluents described above.

Any water-soluble, water-degradable or water-swellable material that can be applied to the core or layer 14 and solidified to form a layer on the core or layer 14 can be used in the layer 22. Suitable water-soluble materials include sorbitol, polyvinylpyrrolidone, polyvinyl alcohol, polyethylene glycol, and carbohydrates such as monosaccharides (e.g., glucose, allose, altrose, mannose, gulose, idose, galactose, talose, ribose, arabinose, xylose, lyxose, erythrose, threose, fucose, rhamnose, and glucosamine), disaccharides (e.g., fructose, sucrose, maltose, lactose), and polysaccharides e.g., starch, agarose, glycogen, cellulose, cellulose derivatives, and chitan). Suitable water-degradable materials include polylactic acids, polyglycolic acids, glycerol esters, polyhydroxyalkanoic acids, glycolipids, glycerides, phospholipids, polyesters, polyethers, polysorbates, lectins, polyureas, polyurethanes, ethylene vinyl acetate copolymers, polyhydroxyalkylates, polyanhydrides, polylactones, polysebacic acids, liposomes, fatty acids, and carnauba wax. Water-swellable materials of the invention include polyvinyl alcohol and derivatives thereof, agarose, polyvinyl pyrrolidone and derivatives thereof, proteins such as gelatin, agar-agar, albumin and collagen, hydroxyproline polymers or oligomers, hydrophilic polyacrylate derivatives, polyethylene oxide and derivatives thereof, carboxyalkylcellulose and derivatives thereof, hydroxylated cellulose derivatives, alginic acid and derivatives thereof, acrylic polymers and copolymers, gums, polyacrylamides, starch graft copolymers, acrylate polymer polysaccharides, sodium starch glycolate, and indene-, styrene-, ethylene-, propylene-, butylene- or isobutylene-maleic anhydride copolymers.

The particles 18 embedded in the outer layer of the powder 20, 26, 32 and 36 contain an anhydrous material capable of binding with water. The particles act as moisture scavengers to minimize premature hydrolysis of the acid releasing agent. Suitable anhydrous materials include sodium sulfate, calcium sulfate, calcium carbonate, ferrous sulfate, magnesium sulfate, calcium chloride, moisture-depleted silica gel, alumina, zeolites, clays such as bentonite and kaolin, potassium permanganate, molecular sieves and oxygen-scavenging salts. The anhydrous particles are commercially available from numerous sources. The anhydrous particles are preferably between about 1 and about 300 microns in diameter.

A powder of particles 10 as shown in FIG. 1a is generally prepared by admixing the core particles containing anions with acid releasing particles to form a particle mixture, sintering the mixture to form a product, cooling the product, and fragmenting the product to form the powder. A powder of the particles 20 as shown in FIG. 1b can be prepared by admixing anhydrous particles with the product and sintering before cooling. A powder of particles 10 can also be prepared by admixing the core particles containing anions with a liquid containing the acid releasing agent to form coated particles, cooling the coated particles, and fragmenting the cooled particles to form the powder. The core particles can be dip-coated in a molten liquid, spray-coated with a liquid solution, or coated by other known processes. A powder of particles 20 as shown in FIG. 1b can be prepared by admixing anhydrous particles with the coated particles before cooling. The acid releasing particles or the liquid containing the acid releasing agent can include a dispersant as described above to prevent agglomeration of the core particles.

A powder of the particles 24 as shown in FIG. 2a can be made by preparing the particles 10 as described above then admixing the particles 10 with a liquid containing a hydrophobic, water-soluble, water-degradable or water-swellable material to form a coated product, cooling the coated product, and fragmenting the coated product to form the powder. A powder of particles 26 as shown in FIG. 2b can be prepared by admixing anhydrous particles with the coated product before cooling. A powder of particles 24 can also be formed by admixing the particles 10 with particles containing a hydrophobic, water-soluble, water-degradable or water-swellable material to form a mixture, sintering the mixture to form a product, cooling the product, and fragmenting the product to form the powder. A powder of the particles 26 as shown in FIG. 2b can be prepared by admixing anhydrous particles with the product and sintering before cooling.

A powder of particles 28 as shown in FIG. 3a is generally prepared by admixing the core particles containing anions with particles containing a hydrophobic, water-soluble, water-degradable or water-swellable material to form a first particle mixture, sintering the first particle mixture to form intermediate particles, admixing the intermediate particles with acid releasing particles to form a second particle mixture, sintering the second particle mixture to form a product, cooling the product, and fragmenting the product to form the powder. A powder of the particles 32 as shown in FIG. 3b can be prepared by admixing anhydrous particles with the product and sintering before cooling. A powder of particles 28 can also be prepared by admixing the core particles containing anions with a liquid containing a hydrophobic, water-soluble, water-degradable or water-swellable material to form coated core particles, cooling the coated core particles, fragmenting the coated core particles to form a core powder, admixing the core powder with a liquid containing the acid releasing agent to form coated particles, cooling the coated particles, and fragmenting the cooled particles to form the powder. A powder of particles 32 as shown in FIG. 3b can be prepared by admixing anhydrous particles with the coated particles before cooling.

A powder of the particles 34 as shown in FIG. 4a can be made by preparing the particles 28 as described above then admixing the particles 28 with a liquid containing a hydrophobic, water-soluble, water-degradable or water-swellable material to form a coated product, cooling the coated product, and fragmenting the coated product to form the powder. A powder of particles 36 as shown in FIG. 4b can be prepared by admixing anhydrous particles with the coated product before cooling. A powder of particles 34 can also be formed by admixing the particles 28 with particles containing a hydrophobic, water-soluble, water-degradable or water-swellable material to form a mixture, sintering the mixture to form a product, cooling the product, and fragmenting the product to form the powder. A powder of the particles 36 as shown in FIG. 4b can be prepared by admixing anhydrous particles with the product and sintering before cooling.

The core particles of the present invention are prepared from commercially available molecular sieves. The molecular sieves are admixed with an aqueous or nonaqueous solution containing anions to allow the anions to sorb into the microstructure of the molecular sieves. Preferably, the salt is disproportionated in the solution. While not being limited thereto, it is believed that anions formed during disproportionation of a salt will bond to the surfaces of the pores within the core and become immobilized until the anions react with hydronium ions. Such immobilization enhances the thermal stability of the powder. Once the anions are intercalated within the molecular sieve microstructure, the molecular sieves are separated from the solution, dried by conventional means, and fragmented to form the core particles. The core particles can be admixed with a hydrophobic, water-soluble, water-degradable or water-swellable material and fragmented before being admixed with the acid releasing agent to prepare the powder of the invention. The core particles are stored in a dry atmosphere.

The powders of the invention can be prepared by the methods described above or by any conventional coating process, such as fluidization. In a fluidization method, the coating material is aerosolized by passing the material through small diameter nozzles into the chamber of the fluidized bed where it can impinge upon the fluidized core particles. Upon contact with the fluidized core particles, the powder is formed as the coating material solidifies. The particles can then be packaged in a dry sealed container. The particles can also be micronized to reduce their particle size and form a finer powder before being packaged. The powders of the invention can also be prepared using mechanical blending, mechanical-fluidized blending and other known powder preparation methods.

The molecular sieves, anhydrous particles and other ingredients can be manufactured by conventional processes and packaged in dry sealed containers, or can be purchased from various sources. The particles and other ingredients are stored in a dry atmosphere before being used in the powder preparation process.

Although the powders can be formulated as described above, it is preferred that the core contains a zeolite and an alkali metal chlorite or alkaline earth metal chlorite for release of chlorine dioxide. The acid releasing layer preferably includes a microcrystalline wax, an oligomeric diluent or a low molecular weight polymeric diluent, and an acid releasing wax, such as propylene glycol monostearate acid releasing wax. The layer 22 preferably contains glucose, sucrose, theose or mannose. The particles are preferably sodium sulfate or calcium sulfate.

The preferred phosphosilicic anhydride acid releasing waxes are generally prepared by melting a carboxylic acid ester of a polyhydric alcohol, admixing phosphorus pentoxide into the melt, then admixing a silicate or silane into the melt, and cooling to solidify the resulting acid releasing wax. The carboxylic acid ester of a polyhydric alcohol is preferably a glycerol ester or glycol ester including, for example, an alkylene glycol carboxylate such as propylene glycol monostearate, glycerol monostearate, or glycerol distearate. Propylene glycol monostearate is most preferred because it does not foam excessively or obstruct nozzles or other fluid transport equipment when preparing the acid releasing wax, or the powders or when incorporating the powders into polymer films or other materials as end products, A substance that is capable of reacting with the silicate or silane to form P—O—Si or C(O)—O—Si bonds in the acid releasing wax can be substituted for phosphorus pentoxide, such as monostearyl diethylphosphate. A process for preparing a phosphosilicic anhydride acid releasing wax using monostearyl diethylphosphate can be performed with reference to Ralph Iler, "Chemistry of Silica: Solubility, Polymerization, Colloid and Surface Properties in Biochemistry," J. Wiley & Sons, N.Y., p. 297 (1979). Preferred silicates or silanes include tetraalkylsilicates such as tetraethyl orthosilicate, alkyl silanes, and monoalkoxy silanes. The preparation of representative acid releasing waxes is described in Examples 1 and 2 below. The process of preparing the acid releasing waxes is further described in copending Wellinghoff et al. U.S. patent application Ser. No. 08/858,860, filed May 19, 1997 and entitled "Compositions for Sustained Release of a Gas," which is incorporated herein by reference.

Applications for the powders are numerous. The powders can be used in most any environment where exposure to moisture can occur. The powders can be formed into solids by molding or sintering. The powders can also be impregnated, melt processed, sintered, or otherwise incorporated into a variety of materials to provide films and coatings for a wide range of end use applications. The powders are particularly useful in preparing any injection molded products, compression molded products, or translucent films. The thermal stability of the powders allows for their use in injection molding processes.

Gas-releasing powders can be used to retard, kill, prevent or control microbiological contamination on a surface of a material, within the material or in the atmosphere surrounding the material by exposing a surface of a material to a powder of the invention, and exposing the surface to moisture to generate and release a biocidal gas from the powder into the atmosphere surrounding the surface. In an alternative embodiment, microbiological contamination is retarded, killed, prevented or controlled on a surface of a material, within the material or in the atmosphere surrounding the material by placing the material adjacent a powder of the invention, and exposing the powder to moisture to release a biocidal gas from the powder into the atmosphere surrounding the material.

Gas-releasing powders can be used to retard, prevent or control biochemical decomposition on a surface of a material or within the material by exposing a surface of a material to a powder of the invention, and exposing the surface to moisture to generate and release a biochemical decomposition-inhibiting gas from the powder into the atmosphere surrounding the surface. In an alternative embodiment, biochemical decomposition is retarded, prevented or controlled on a surface of a material or within the material by placing the material adjacent a powder of the invention, and exposing the powder to moisture to release a biochemical decomposition-inhibiting gas from the powder into the atmosphere surrounding the material. The material is preferably produce or other food. The food is preferably stored or transported in modified atmosphere packaging to extend the shelf life of the food by retarding, preventing or controlling biochemical decomposition or microbiological contamination.

The gas-releasing powders can also be used to control respiration of a material by exposing a surface of a material to a powder of the invention, and exposing the surface to moisture to generate and release a respiration-controlling gas from the powder into the atmosphere surrounding the surface. In an alternative embodiment, respiration of a material is controlled by placing the material adjacent a powder of the invention, and exposing the powder to moisture to release a respiration-controlling gas from the powder into the atmosphere surrounding the material. The material is preferably fruits, vegetables, flowers, or other plants. Control of respiration of foods and flowers is generally accomplished by storing and transporting the food or flowers in modified atmosphere packaging.

The gas-releasing powders can also be used to deodorize a surface of a material or the atmosphere surrounding the material by exposing a surface of a material to a powder of the invention, and exposing the surface to moisture to generate and release a deodorizing gas from the powder into the atmosphere surrounding the surface. In another embodiment, a surface of a material or the atmosphere surrounding the material is deodorized by placing the material adjacent to the powder, and exposing the powder to moisture to release a deodorizing gas from the powder into the atmosphere surrounding the material.

The gas-releasing powders can also be used to retard, prevent or control chemotactic attraction of an organism to a material by exposing a surface of a material to a powder of the invention, and exposing the surface to moisture to generate and release an odor-masking or odor-neutralizing gas from the powder into the atmosphere surrounding the surface. In another embodiment, chemotactic attraction of an organism to a material is retarded, prevented or controlled by placing the material adjacent to the powder, and exposing the powder to moisture to release an odor-masking or odor-neutralizing gas from the powder into the atmosphere surrounding the material.

In the above methods, the surface of the material can be impregnated with the powder, the powder can be admixed with the material, the powder can be enclosed within a gas-permeable container, or the material and the powder can be enclosed within a container. When the powder is enclosed within a container, the container can be hermetically sealed, or partially sealed such that some gas leaks from the container.

The chlorine dioxide-releasing powder, for example, can be impregnated into containers used to store food products, soap, laundry detergent, documents, clothing, paint, seeds, medical instruments, devices and supplies, personal care products, medical or biological waste, athletic shoes, ostomy bags, footwear, and refuse. A packet, sachet bag, "tea bag"

or other gas-permeable container of the powder can be included in a storage container to provide a chlorine dioxide microatmosphere upon activation. The chlorine dioxide-releasing powder can also be impregnated into a paper or polymeric material (e.g., a shower mat, shoe liners, inserts or insoles, bandage material, a meat cutting board, a food wrapper, a food packaging tray, or a seed packet); formed into porous parts to sterilize water; admixed with a material to create a microatmosphere of chlorine dioxide about the material (e.g., soil); or admixed with other powders to kill microorganisms or deodorize (e.g., foot powders, bath powders, powders used in treating jock itch).

In addition to deodorization to neutralize malodors, the powders can be used to retard, prevent or control chemotaxis (i.e., the attraction of a living organism to a chemical substance). For example, odors from food can attract insects to the food. When the food is adjacent a powder of the invention that releases an odor-masking gas, the odor released from food is indistinct or imperceptible to the insects. The powders of the invention can also be used to release an odor-neutralizing gas so that the odor released from food is reduced or eliminated and insects are not attracted to the food.

The powders are also especially suitable for use in animal feeds. During preparation and handling, animal feeds for monogastric animals, such as chickens, swine, cats, dogs, rabbits, rats, mice and the like, are often contaminated with bacteria which infect the animal. If the powders of the present invention are formed from edible components, including edible protein coatings, the powders can be incorporated into the animal feed during any stage of production, before transportation or storage of the feed, or before use of the feed so that the chlorine dioxide will reduce or eliminate the bacteria within the feed. The controlled, sustained release powders also reduce the bacterial load in the intestines of such monogastric animals.

The following examples are presented to describe preferred embodiments and utilities of the present invention and are not meant to limit the present invention unless otherwise stated in the claims appended hereto.

EXAMPLE 1

In order to make a hydrophobic propylene glycol monostearate acid releasing wax (PGMS) on a laboratory scale, propylene glycol monostearate (200 g) was melted in a dry, stoppered, 2-liter schlenk at 50–60° C. using a heating mantle. The melt was stirred at constant: temperature under reduced pressure for three to four hours to remove residual moisture. When bubbling of the melt under vacuum ceased, the schlenk was flushed and maintained with dry nitrogen gas.

Phosphorus pentoxide (27.7 g) was loaded into a powder addition funnel in a glove bag continuously purged with dry nitrogen. The funnel was connected to the schlenk under flowing nitrogen, and the phosphorus pentoxide was gradually added to the melt using a screw feeder over three or four hours as the melt was stirred rapidly at 50–60° C. under dry nitrogen. After the addition, the melt was stirred under dry nitrogen gas for at least four hours.

Tetraethyl orthosilicate (TEOS; 39 ml) was then added slowly over 40 minutes using an addition funnel. Ethanol by-product was vented through a septum and needle inserted at the top of the addition funnel. After the TEOS addition, remaining ethanol was pumped off under reduced pressure for about 12 hours while minimizing foaming and maintaining a temperature sufficient to volatilize ethanol condensed on the schlenk walls. The resulting propylene glycol monostearate acid releasing wax was then allowed to solidify at room temperature in the glove bag under dry nitrogen.

EXAMPLE 2

In order to make a hydrophobic propylene glycol monostearate acid releasing wax on a commercial scale, propylene glycol monostearate (1225.5 lbs.) was melted at 55° C. using oil heating in a stainless steel stirred tank jacketed reactor with internal cooling coils and a reflux condenser/receiver system. Powdered phosphorus pentoxide (170.2 lbs.) was introduced gradually over three to four hours with cooling. After the reaction proceeded for four to six hours at 55° C., tetraethyl orthosilicate (221.3 lbs) was added to the tank and allowed to react for 12 hours under vacuum. The propylene glycol monostearate acid releasing wax was collected from the bottom of the reactor and allowed to solidify at room temperature.

EXAMPLE 3

Chlorite impregnated core particles were prepared on a laboratory scale. Zeolite particles (clinoptiloite available as Zeo Crystal™ from ZeoCrystal Industries, Crestwood, Ill.) were suspended in aqueous solutions of sodium chlorite, some of which contained a base (calcium carbonate). The zeolite particles were removed from the solution after five to ten minutes and dried in a vacuum oven at 110° C. for four hours. The dried particles were fragmented with a mortar and pestle to provide a powder. Compositions A-I were prepared from the ingredients listed in Table 1 below.

TABLE 1

| Comp. | Form of Zeolite | Zeolite wt. (g) | Chlorite type | Chlorite solution wt. (g) | Calcium carbonate wt. (g) |
|---|---|---|---|---|---|
| A | Powder | 22 | AD[1] | 10 | 20 |
| B | Powder | 24 | AD | 11 | 5 |
| C | Powder | 25 | AD | 11 | 0 |
| D | Powder | 23 | Exspor[2] | 10 | 5 |
| E | Powder | 22 | Exspor | 10 | 0 |
| F | Powder | 25 | NCS[3] | 11 | 5 |
| G | Powder | 20 | NCS | 10 | 0 |
| H | Rock | 20 | AD | 10 | 5 |
| I | Rock | 25 | AD | 11 | 0 |

[1]Anthium Dioxide (5% stabilized sodium chlorite solution from International Dioxide)
[2]Exspor ™ (1.52% stabilized sodium chlorite solution from Alcide Corp.)
[3]NCS (5% sodium chlorite solution of technical grade (i.e., 4% sodium chlorite content) from Aldrich)

Compositions A-I were each sprayed with water droplets. A moistened chlorine test strip paper (Aquacheck™, Environmental Test Systems) was used to determine whether chlorine dioxide was released. The test strip did not change colors during one hour of observation, indicating that the zeolite core particles did not spontaneously release chlorine dioxide upon exposure to moisture.

EXAMPLE 4

Chlorine dioxide-releasing powders were prepared on a laboratory scale. The zeolite core particles A–G of Example 3 were admixed with particles of either the PGMS acid releasing wax as prepared in Example 2 or 100% oxalic acid. The particle mixture was sintered in a test tube for a few seconds at 50–70° C. then cooled in ice before being pulverized in a mortar and pestle to form a powder. The powder was sprayed with drops of moisture and chlorine dioxide release was determined using moistened chlorine test strip papers (Aquacheck™, Environmental Test Systems). The ingredients of the powder and the time of color change of the test strip are indicated in Table 2.

TABLE 2

| Composition | Zeolite Wt. (g) | Acid Type | Acid Wt. (g) | Time to color change (min) |
| --- | --- | --- | --- | --- |
| A | 1 | PGMS | 1 | >1* |
| B | 1 | PGMS | 1 | >1* |
| C | 1 | PGMS | 1 | <1 |
| A | 1 | Oxalic | 1 | Immediate* |
| B | 1 | Oxalic | 1 | Immediate* |
| C | 1 | Oxalic | 1 | Immediate |
| D | 1 | PGMS | 1 | >1* |
| E | 1 | PGMS | 1 | <1 |
| F | 1 | PGMS | 1 | >1* |
| G | 1 | PGMS | 1 | <1 |

*Bubbling was observed, indicating release of carbon dioxide due to reaction of hydronium ions with calcium carbonate The oxalic acid/zeolite powders immediately released chlorine dioxide regardless of whether the powder included a base. The PGMS/zeolite powders of the invention released chlorine dioxide gas within minutes of exposure to moisture. Initial gas release was delayed by the presence of calcium carbonate (i.e., a base). Carbon dioxide was also released from powders that included calcium carbonate. The total time during which gas was released from the powder was not determined.

EXAMPLE 5

Chlorine dioxide-releasing powders including a water-soluble layer surrounding the core particles were prepared on a laboratory scale. The zeolite core particles H-I of Example 3 were admixed with molten glucose, cooled and crushed to form coated core particles. The coated core particles were admixed with PGMS powder before the core particles were completely cooled such that the PGMS powder adhered to the core particles. The product was crushed into a powder. The powder was sprayed with drops of moisture and chlorine dioxide release was determined using moistened chlorine test strip papers (Aquacheck™, Environmental Test Systems). The ingredients of the powder and the time of color change of the test strip are indicated in Table 3.

TABLE 3

| Comp. | Zeolite wt. (g) | Glucose wt. (g) | Acid wt. (g) | Time to color change (min) |
| --- | --- | --- | --- | --- |
| H | 0.11 | 0.1 | 0 | No change |
| I | 0.15 | 0.1 | 0 | No change |
| H | 0.19 | 0.1 | 0.21 | >3* |
| I | 0.25 | 0.1 | 0.30 | >2 |

*Bubbling was observed, indicating release of carbon dioxide due to reaction of hydronium ions with calcium carbonate The glucose-containing powders did not release chlorine dioxide upon exposure to moisture until after several minutes. The glucose delayed chlorine dioxide release. Chlorine dioxide release was further delayed and carbon dioxide was also released in powders containing calcium carbonate. The total time during which gas was released from the powder was not determined.

U.S. Pat. Nos. 5,360,609, 5,631,300, 5,639,295, 5,650,446, and U.S. patent application Ser. Nos. 08/016,904, 08/465,086, 08/461,716, 08/461,304, 08/462,039, 08/682, 318, 08/724,907, 08/858,859 and 08/858,860 are incorporated herein by reference in their entirety.

While the invention is susceptible to various modifications and alternative forms, specific embodiments thereof have been shown by way of example in the drawings and have been described herein in detail. It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A powder for sustained release of a gas comprising:
   a core containing a molecular sieve and anions that are capable of reacting to generate a gas; and
   a layer containing an acid releasing agent on an outer surface of the core;
   the core and the layer being substantially free of water, and the core being capable of generating and releasing a gas after hydrolysis of the acid releasing agent.

2. The powder of claim 1 wherein the molecular sieve is a natural or synthetic zeolite, a crystalline aluminophosphate, a ferricyanide or a heteropolyacid.

3. The powder of claim 1 wherein the core contains a base.

4. The powder of claim 3 wherein the base is an alkali metal bicarbonate, an alkali metal carbonate, an alkaline-earth metal bicarbonate, an alkaline-earth metal carbonate, a bicarbonate salt of a transition metal ion or a protonated primary, secondary, tertiary or quaternary amine, a carbonate salt of a transition metal ion or a protonated primary, secondary, tertiary or quaternary amine, an alkali metal hydroxide, an alkaline-earth metal hydroxide, an hydroxide salt of a transition metal ion or a protonated primary, secondary, tertiary or quaternary amine, an alkali metal biphosphate, an alkali metal phosphate, an alkaline-earth metal biphosphate, an alkaline-earth metal phosphate, a biphosphate salt of a transition metal ion or a protonated primary, secondary, tertiary or quaternary amine, a phosphate salt of a transition metal ion or a protonated primary, secondary, tertiary or quaternary amine, an alkali metal bisulfate, an alkali metal sulfate, an alkaline-earth metal bisulfate, an alkaline-earth metal sulfate, a bisulfate salt of a transition metal ion or a protonated primary, secondary, tertiary or quaternary amine, a sulfate salt of a transition metal ion or a protonated primary, secondary, tertiary or quaternary amine, an alkali metal sulfonate, an alkaline-earth metal sulfonate, or a sulfonate salt of a transition metal ion or a protonated primary, secondary, tertiary or quaternary amine, an alkali metal borate, an alkaline-earth metal borate, or a borate salt of a transition metal ion or a protonated primary, secondary, tertiary or quaternary amine.

5. The powder of claim 1 wherein the core contains chlorite anions, bisulfite anions, cyanide anions, nitrite anions, hypochlorite anions, or hydrosulfide anions.

6. The powder of claim 5 wherein the core contains an alkali metal chlorite, an alkaline-earth metal chlorite, a chlorite salt of a transition metal ion or a protonated primary, secondary, tertiary or quaternary amine, an alkali metal bisulfite, an alkaline-earth metal bisulfite, a bisulfite salt of a transition metal ion or a protonated primary, secondary, tertiary or quaternary amine, an alkali metal hydrosulfide, an alkaline-earth metal hydrosulfide, a hydrosulfide salt of a transition metal ion or a protonated primary, secondary, tertiary or quaternary amine, an alkali metal nitrite, an alkaline-earth metal nitrite, a nitrite salt of a transition metal ion or a protonated primary, secondary, tertiary or quaternary amine, an alkali metal hypochlorite, an alkaline-earth metal hypochlorite, a hypochlorite salt of a transition metal ion or a protonated primary, secondary, tertiary or quaternary amine, an alkali metal cyanide, an alkaline-earth metal cyanide, or a cyanide salt of a transition metal ion or a protonated primary, secondary, tertiary or quaternary amine.

7. The powder of claim 5 wherein the core contains a sodium, potassium, calcium, lithium or ammonium salt of a chlorite, bisulfite, hydrosulfide, nitrite, hypochlorite, or cyanide.

8. The powder of claim 1 wherein the gas is chlorine dioxide, sulfur dioxide, hydrogen sulfide, hydrocyanic acid, nitrogen dioxide, nitric oxide, dichlorine monoxide, or chlorine.

9. The powder of claim 1 wherein the layer containing the acid releasing agent includes a microcrystalline wax, a paraffin wax, a synthetic wax, a polymer or an oligomer.

10. The powder of claim 1 further including a hydrophobic, water-soluble, water-degradable or water-swellable layer on an outer surface of the layer containing the acid releasing agent, the hydrophobic, water-soluble, water-degradable or water-swellable layer being substantially free of water.

11. The powder of claim 10 wherein the hydrophobic, water-soluble, water-degradable or water-swellable layer contains a microcrystalline wax, a paraffin wax, a synthetic wax, a polymer, sorbitol, a carbohydrate, a protein, a glycerol ester, a glycolipid, a glyceride, a phospholipid, lectins, a liposome, a fatty acid, a wax, alginic acid, or a gum.

12. The powder of claim 1 wherein the layer containing the acid releasing agent includes a dispersant selected from the group consisting of an amide of a carboxylate, polyvinylpyrrolidone copolymer, polyvinyl acetate, polyethylene glycol, polyvinyl alcohol, and metal carboxylate.

13. The powder of claim 1 wherein the acid releasing agent is an acid releasing wax, an acid releasing polymer, or an acid releasing oligomer.

14. The powder of claim 1 wherein the acid releasing agent includes a carboxylic acid, an ester, an anhydride, an acyl halide, phosphoric acid, a phosphate ester, a trialkylsilyl phosphate ester, a dialkyl phosphate, sulfonic acid, a sulfonic acid ester, a sulfonic acid chloride, a phosphosilicic anhydride, or a phosphosilicate.

15. The powder of claim 1 further including particles in contact with the layer containing the acid releasing agent, the particles being substantially free of water and containing an anhydrous material capable of binding with water.

16. The powder of claim 15 wherein the particles contain sodium sulfate, calcium sulfate, calcium carbonate, ferrous sulfate, magnesium sulfate, calcium chloride, moisture-depleted silica gel, alumina, zeolites, bentonite clay, kaolin clay, potassium permanganate, a molecular sieve or an oxygen-scavenging salt.

17. The powder of claim 1 wherein at least about $1.0 \times 10^{-6}$ gram gas/cm$^3$ is released from the powder for a period of at least one week after hydrolysis of the acid releasing agent.

18. The powder of claim 1 wherein the layer containing the acid releasing agent is continuous.

19. The powder of claim 10 wherein the hydrophobic, water-soluble, water-degradable or water-swellable layer is continuous.

20. A process for preparing a powder providing sustained release of a gas, the process comprising admixing molecular sieve particles containing anions with an acid releasing agent to form a product, and fragmenting the product to form a powder, the powder comprising a core containing a molecular sieve and anions that are capable of reacting to generate a gas, and a layer containing an acid releasing agent on an outer surface of the core, the core and the layer being substantially free of water and the core being capable of generating and releasing the gas after hydrolysis of the acid releasing agent.

21. The process of claim 20 wherein the molecular sieve particles are prepared by admixing molecular sieves with an aqueous or nonaqueous solution containing the anions, separating the molecular sieves from the solution, drying the molecular sieves, and fragmenting the molecular sieves to form the molecular sieve particles.

22. The process of claim 20 wherein the molecular sieve particles are admixed with a hydrophobic material, a water-soluble material, a water-degradable material, or a water-swellable material and fragmented before being admixed with the acid releasing agent.

23. The process of claim 20 wherein the acid releasing agent is a particulate and the product is sintered before being fragmented.

24. The process of claim 20 wherein the powder is admixed with a hydrophobic material, a water-soluble material, a water-degradable material, or a water-swellable material and fragmented to delay release of the gas from the powder.

25. The process of claim 20 wherein a dispersant, a hydrophobic material, a water-soluble material, a water-degradable material, or a water-swellable material is admixed with the acid releasing agent before the acid releasing agent is admixed with the molecular sieve particles.

26. The process of claim 20 wherein the powder is admixed with particles containing an anhydrous material capable of binding with water, the particles being substantially free of water.

27. A method of retarding, killing, preventing or controlling microbiological contamination on a surface of a material, within the material or in the atmosphere surrounding the material, comprising exposing a surface of a material to a powder of claim 1, and exposing the surface to moisture to generate and release a biocidal gas from the powder into the atmosphere surrounding the surface.

28. A method of retarding, killing, preventing or controlling microbiological contamination on a surface of a material, within the material or in the atmosphere surrounding the material, comprising placing a material adjacent a powder of claim 1, and exposing the powder to moisture to release a biocidal gas from the powder into the atmosphere surrounding the material.

29. A method of retarding, preventing or controlling biochemical decomposition on a surface of a material or within the material comprising exposing a surface of a material to a powder of claim 1, and exposing the surface to moisture to generate and release a biochemical decomposition-inhibiting gas from the powder into the atmosphere surrounding the surface.

30. A method of retarding, preventing or controlling biochemical decomposition on a surface of a material or within the material comprising placing the material adjacent a powder of claim 1, and exposing the powder to moisture to release a biochemical decomposition-inhibiting gas from the powder into the atmosphere surrounding the material.

31. A method of controlling respiration of a material comprising exposing a surface of a material to a powder of claim 1, and exposing the surface to moisture to generate and release a respiration-controlling gas from the powder into the atmosphere surrounding the surface.

32. A method of controlling respiration of a material comprising placing the material adjacent a powder of claim 1, and exposing the powder to moisture to release a respiration-controlling gas from the powder into the atmosphere surrounding the material.

33. A method of deodorizing a surface of a material or the atmosphere surrounding the material, comprising exposing a surface of a material to a powder of claim 1, and exposing the surface to moisture to generate and release a deodorizing gas from the powder into the atmosphere surrounding the surface.

34. A method of deodorizing a surface of a material or the atmosphere surrounding the material, comprising placing a material adjacent a powder of claim 1, and exposing the powder to moisture to release a deodorizing gas from the powder into the atmosphere surrounding the material.

35. A method of retarding, preventing or controlling chemotactic attraction of an organism to a material, comprising exposing a surface of a material to a powder of claim 1, and exposing the surface to moisture to generate and release an odor-masking gas or an odor-neutralizing gas from the powder into the atmosphere surrounding the surface.

36. A method of retarding, preventing or controlling chemotactic attraction of an organism to a material, comprising placing a material adjacent a powder of claim 1, and exposing the powder to moisture to release an odor-masking gas or an odor-neutralizing gas from the powder into the atmosphere surrounding the material.

\* \* \* \* \*